US012636410B2

(12) United States Patent
Yu et al.

(10) Patent No.: US 12,636,410 B2
(45) Date of Patent: May 26, 2026

(54) TISSUE RESTORATION COMPOSITION

(71) Applicant: DEXLEVO INC., Seoul (KR)

(72) Inventors: Jae Won Yu, Seoul (KR); Myung Seob Shim, Seoul (KR); Jun Bae Kim, Daejeon (KR)

(73) Assignee: DEXLEVO INC., Seoul (KR)

( * ) Notice: Subject to any disclaimer, the term of this patent is extended or adjusted under 35 U.S.C. 154(b) by 727 days.

(21) Appl. No.: 17/777,225

(22) PCT Filed: Nov. 23, 2020

(86) PCT No.: PCT/KR2020/016617
§ 371 (c)(1),
(2) Date: May 16, 2022

(87) PCT Pub. No.: WO2021/101353
PCT Pub. Date: May 27, 2021

(65) Prior Publication Data
US 2022/0401628 A1 Dec. 22, 2022

(30) Foreign Application Priority Data

Nov. 22, 2019 (KR) ........................ 10-2019-0151669

(51) Int. Cl.
*A61L 27/60* (2006.01)
*A61L 27/18* (2006.01)
(Continued)

(52) U.S. Cl.
CPC ............... *A61L 27/60* (2013.01); *A61L 27/18* (2013.01); *A61L 27/50* (2013.01); *C08G 63/08* (2013.01);
(Continued)

(58) Field of Classification Search
CPC .......... A61L 27/60; A61L 27/18; A61L 27/50; A61L 2400/06; A61L 2430/34; C08G 63/08; C08G 63/664
See application file for complete search history.

(56) References Cited

U.S. PATENT DOCUMENTS

| | | | |
|---|---|---|---|
| 8,329,856 B2 | 12/2012 | Kim et al. | |
| 9,982,090 B2 | 5/2018 | Choi et al. | |
| 2016/0045645 A1 | 2/2016 | Kim et al. | |

FOREIGN PATENT DOCUMENTS

| | | | |
|---|---|---|---|
| EP | 1641471 B1 | 12/2006 | |
| EP | 1493404 B1 | 3/2015 | |

(Continued)

OTHER PUBLICATIONS

Kim et al., "Preparation of poly(ethylene glycol)-block-poly(caprolactone)copolymers and their applications as thermo-sensitive materials", Journal of Biomedical Materials Research , Part A. vol. 70A, issue 1, May 10, 2004. (Year: 2004).*

(Continued)

*Primary Examiner* — Jianfeng Song
(74) *Attorney, Agent, or Firm* — Paratus Law Group, PLLC

(57) ABSTRACT

A tissue restoration composition in a colloidal phase, includes a copolymer in which a hydrophobic biocompatible polymer and a hydrophilic biocompatible polymer are polymerized and which is dispersed in water. The colloidal phase has increased viscosity by heating the copolymer dispersed in water. The colloidal phase has a viscosity, by the heating, of 20-200,000 cP.

6 Claims, 7 Drawing Sheets

(51) Int. Cl.
    *A61L 27/50*     (2006.01)
    *C08G 63/08*     (2006.01)
    *C08G 63/664*     (2006.01)

(52) U.S. Cl.
    CPC ........ *C08G 63/664* (2013.01); *A61L 2400/06*
        (2013.01); *A61L 2430/34* (2013.01)

(56)           References Cited

FOREIGN PATENT DOCUMENTS

| | | | |
|---|---|---|---|
| KR | 10-0412227 | B1 | 12/2003 |
| KR | 10-0832552 | B1 | 5/2008 |
| KR | 10-2014-0072008 | A | 6/2014 |
| KR | 10-2015-0007051 | A | 1/2015 |
| KR | 10-2016-0033897 | A1 | 3/2016 |
| KR | 10-1689798 | B1 | 12/2016 |
| KR | 101689357 | B1 * | 12/2016 |
| KR | 10-2144479 | B1 | 8/2020 |
| KR | 10-2251192 | B1 | 5/2021 |
| WO | WO 2008/014561 | A1 | 2/2008 |
| WO | WO 2009/106641 | A2 | 9/2009 |

OTHER PUBLICATIONS

Moon Suk Kim et al., "Preparation of Thermosensitive Diblock Copolymers Consisting of MPEG and Polyesters", Macromolecules, May 2, 2006, pp. 3099-3102, vol. 39, No. 9.

Yun Mi Kang et al., "A biodegradable, injectable, gel system based on MPEG-b-(PCL-ran-PLLA) diblock copolymers with an adjustable therapeutic window", Biomaterials, Dec. 22, 2009, pp. 2453-2460, vol. 31.

Korean Office Action for related KR Application No. 10-2020-0158100 mailed Jul. 13, 2022 from Korean Intellectual Property Office.

Korean Office Action for related KR Application No. 10-2020-0158100 mailed Mar. 29, 2023 from Korean Intellectual Property Office.

Australian Examination Report for related AU Application No. 2020387490 mailed Jul. 13, 2023 from Australian Government IP Australia.

Indian Examination Report for related IN Application No. 202237028056 mailed Feb. 15, 2023 from Indian Patent Office.

Hyo Won Seo et al., "Injectable intratumoral hydrogel as 5-fluorouracil drug depot", Biomaterials, Jan. 21, 2013, pp. 2748-2757, vol. 34.

Hoon Hyun et al., "Thermo-Responsive Injectable MPEG-Polyester Diblock Copolymers for Sustained Drug Release", Polymers, Oct. 23, 2014, pp. 2670-2683, vol. 6.

Ju Young Lee et al., "In vivo efficacy of paclitaxel-loaded injectable in situ-forming gel against subcutaneous tumor growth", International Journal of Pharmaceutics, Mar. 16, 2010, pp. 51-56, vol. 392.

Junde Guo et al., "Biotribological application of poly(ε-caprolactone)-poly(ethylene glycol)-poly(ε-caprolactone) hydrogel as an efficient carrier with slow-release lubrication effect", Journal of Materials Science, Jul. 6, 2017, pp. 12054-12066, vol. 52.

Written Opinion submitted for KR Application No. 10-2014-0124689 and open to the public on Oct. 5, 2016 by Korean Intellectual Property Office.

International Search Report for PCT/KR2020/016617 mailed Feb. 24, 2021 from Korean Intellectual Property Office.

Klaus Laeschke, "Biocompatibility of Microparticles into Soft Tissue Fillers", Seminas in Cutaneous Medicine and Surgery, 2004, pp. 214-217.

USFDA, "Injectable Dermal Filler for Sculptra Aesthetic", Summary of Safety and Effectiveness Data, Jul. 28, 2009, pp. 1-20, PMA No. P030050/S2, sanofi-aventis U.S., LLC.

USFDA, "Injectable Dermal Filler for Sculptra™M", Summary of Safety and Effectiveness Data, Aug. 3, 2004, pp. 1-11, PMA No. P030050, Dermik Laboratories.

S. S. Shah et al., "Poly-DL-lactic acid: Polyethylene glycol block copolymers. The influence of polyethylene glycol on the degradation of poly-DL-lactic acid", Journal of Biomaterials Science, Polymer Edition, 1994, pp. 421-431, vol. 5, No. 5.

Rhoda S. Narins et al., "A randomized study of the efficacy and safety of injectable poly-L-lactic acid versus human-based collagen implant in the treatment of nasolabial fold wrinkles", Journal of the American Academy of Dermatology, Mar. 2010, pp. 448-462, vol. 62, No. 3.

Rosemarie Mazzuco et al., "Poly-L-Lactic Acid for Neck and Chest Rejuvenation", Dermatologic Surgery, Aug. 2009, pp. 1228-1237, vol. 35, No. 8.

Natalie Huang Attenello et al., "Injectable Fillers: Review of Material and Properties", Facial Plastic Surgery, 2015, pp. 29-34, vol. 31, No. 1.

Victor Lacombe, "Sculptra: A Stimulatory Filler", Facial Plastic Surgery, 2009, pp. 95-99, vol. 25, No. 2.

Melanie D. Palm et al., "The "skinny"on Sculptra: a practical primer to volumization with poly-L-lactic acid" (partial), Journal of Drugs in Dermatology, Sep. 2012, pp. 1046-1052, vol. 11, No. 9.

Kyle Brewer et al., "Thermoresponsive Poly(ε-Caprolactone)-Poly(Ethylene/Propylene Glycol) Copolymers as Injectable Hydrogels for Cell Therapies", Polymers, Feb. 7, 2020, pp. 1-19, vol. 12, No. 367.

Flávia as Addor et al., "Injectable Polyethylene Glycol Gel as Dermal Filler: 01 Year Clinical and Ultrasound Follow-Up", Journal of Clinical & Experimental Dermatology Research, Feb. 22, 2016, pp. 1-5, vol. 7, No. 2.

Min Fan et al., "Dexamethasone-Loaded Poly(D, L-lactic acid) Microspheres/Poly(ethylene glycol)-Poly(ε-caprolactone)-Poly(ethylene glycol) Micelles Composite for Skin Augmentation", Journal of Biomedical Nanotechnology, 2014, pp. 592-602, vol. 10, No. 4.

Nava Shpaisman et al., "One-Step Synthesis of Biodegradable Curcumin-Derived Hydrogels as Potential Soft Tissue Fillers after Breast Cancer Surgery", Biomacromolecules, Jun. 16, 2012, pp. 2279-2286, vol. 13.

Stefano Santoro et al., "Rheological properties of cross-linked hyaluronic acid dermal fillers", Journal of Applied Biomaterials and Biomechanics, 2011, pp. 127-136, vol. 9, No. 2.

* cited by examiner (a) Comparative Example (b) Example 3
(using copolymer prepared
by Preparation Example 5)

TISSUE RESTORATION COMPOSITION

CROSS-REFERENCE TO PRIOR APPLICATIONS

This application is a National Stage Patent Application of PCT International Patent Application No. PCT/KR2020/016617 (filed on Nov. 23, 2020) under 35 U.S.C. § 371, which claims priority to Korean Patent Application No. 10-2019-0151669 (filed on Nov. 22, 2019), which are all hereby incorporated by reference in their entirety.

BACKGROUND

The present invention relates to a tissue restoration composition, and more particularly, a tissue restoration composition using polymers.

As a social structure is changing and the population is increasing, the number of patients with burns, a decubitus, trauma, plastic surgery, intractable ulcer, diabetic dermonecrosis, etc. is gradually increasing. Thus, a method for treating damaged skins is being developed accordingly. Even 30 years ago, patients whose damaged skin occupies 60% or more of a body surface area by burns usually died of sepsis, but recently improved artificial skin can protect dehydration and infections, and therefore, mortality rate can be significantly decreased. The artificial skin is largely divided into wound dressing and cultured skin.

The wound dressing is applicable to topical wounds or wounds depth less severe, and the wound dressing plays a role in protecting a wound during a period of time until skin grafting is possible or during 3-4 weeks until auto cultured skin is completed, and thereby easily applying cultured skin.

The cultured skin is used in treatment for minimizing scar tissue in the case of severe skin loss or extensive wound. The cultured skin is grafted for permanent engraftment after fully proliferating dermal cells using cell culture techniques. For cultured skin, many reviews for safety are required through a test of bacteria, fungi, endotoxicity, and mycoplasma, and it is inconvenient in that the cultured skin should be manufactured after confirming safety through various viruses [HIV 1 & 2, HTLVII & IIII, CMV lgM, Hepatitis B & C, and adenovirus] test. Further, in the case of grafting skin from human corpses, there are a problem of unknown source thereof and a disadvantage that, it is impossible to thermally treat the component in the human body in a processing treatment, the fatal viruses aforementioned cannot be sterilized up to 100%. Furthermore, since it takes at least one week to culture cells and graft the same, it is hard to be used for patients requiring first aid.

Meanwhile, the wound dressing has an advantage that the wound dressing can be extensively applied and easily treated relative to the cultured skin, and can be applied to patients requiring first aid. The wound dressing, however, is hard to be grafted permanently since the wound dressing is used for temporary covering. In addition, the wound dressing of natural polymer, such as chitin, chitosan, or collagen has a low mechanical strength, is expensive, and is hard to mass produce; and the wound dressing of synthetic polymer, such as silicone or polyurethane has a disadvantage that the wound dressing has low affinity with cells and no adhesion to a wound site.

Recently, several products using hyaluronic acid gel have been developed, but hyaluronic acid is resorbed very rapidly in the living body between 2 weeks and 2 months, thereby causing a problem. Thus, a product the resorbing period of which is extended by crosslinking hyaluronic acid and crosslinkable materials with each other, as disclosed in Korean Patent Laid-open Publication No. 10-2004-0072008 is commercially available. Such a crosslinked product, however, is also reported to have a problem due to toxicity of crosslinkable materials.

Due to these problems, recently several products for tissue repair treatment using biodegradable polymers are developed, and these products are developed and used as a filler formulation using the existing biocompatible polymers, or a formulation which is dispersed through media having viscosity after processing polymers insoluble in water into microparticles. A formulation in which 20-50 μm of poly lactic acid (PLA) particles are dispersed in carboxymethylcellulose (CMC) aqueous solution, or a formulation in which 20-50 μm of polycaprolactone (PCL) particles are dispersed in CMC and glycerin aqueous solution has been used; however, this causes an inconvenience on a procedure because microparticles to be blocked by a needle during injection, and also arises a problem in that microparticles are not uniformly dispersed, so that tissues are not uniformly repaired.

Further, according to Klaus Laeschke, "Biocompatibility of Microparticles into Soft Tissue Fillers," "Semin Cutan Med Surg 23," 2004, 214-217, a polymer-based tissue repair treatment product should have a particle diameter of 40 μm or more to exhibit long-lasting effects, while avoiding phagocytosis in vivo. However, using the formulation having a particle diameter of 20 μm or more results in an inconvenience on a procedure because microparticles are blocked by a needle, and causes a problem in that microparticles are not uniformly dispersed, so that tissues are not uniformly repaired.

Development of a product for tissue repair treatment to solve such problems above is needed urgently.

SUMMARY

The present invention has been made keeping in mind the above problems occurring in the related art, and directed to providing a tissue restoration composition using non-toxic polymers.

The present invention provides a tissue restoration composition in a colloidal phase, including a copolymer in which a hydrophobic biocompatible polymer and a hydrophilic biocompatible polymer are polymerized and which is dispersed in water, wherein the colloidal phase has increased viscosity by heating the copolymer dispersed in water.

Moreover, the present invention provides a tissue restoration composition, wherein the colloidal phase has a viscosity, by the heating, of 20-200,000 cP.

Further, the present invention provides a tissue restoration composition, wherein the composition may have a range of K factor represented by the following equation 1 is 0.01-5:

$$K=(m_{100}*M_h^2*10)/(M_1*HLB^2) \qquad \text{<Equation 1>}$$

In equation 1, $m_{100}$ is the number of moles of polymers in 100 g of an aqueous solution, $M_h$ is the molecular weight of a hydrophilic part, $M_1$ is the molecular weight of a hydrophobic part, and HLB is represented by the following equation 2:

$$HLB=20*M_h/M \qquad \text{<Equation 2>}$$

In equation 2, $M_h$ is the molecular weight of the hydrophilic part, and M is the total molecular weight.

In addition, the present invention provides a tissue restoration composition, wherein the value of HLB may be 0.1-20 in the equation 2.

Furthermore, the present invention provides a tissue restoration composition, wherein the hydrophobic biocompatible polymer may be at least any one polymer selected from the group consisting of polyglycolic acid, polycaprolactone, poly lactic acid, polydioxanone, poly(trimethylene carbonate), polyhydroxybutyrate, and a copolymer including the same.

Additionally, the present invention provides a tissue restoration composition, wherein the hydrophilic biocompatible polymer may be at least any one polymer selected from the group consisting of methoxy polyethylene glycol, dihydroxy polyethylene glycol, mono-alkoxy polyethylene glycol, and polyethylene glycol.

Moreover, the present invention provides a tissue restoration composition, wherein the bonding structure of the copolymer may include the structure of the following formula 1, formula 2, or formula 3:

$$X—Y \qquad \text{[Formula 1]}$$

$$Y—X—Y \qquad \text{[Formula 2]}$$

$$X—Y—X \qquad \text{[Formula 3]}$$

In formulae 1-3, X is a hydrophilic biocompatible polymer, and Y is a hydrophobic biocompatible polymer.

Further, the present invention provides a tissue restoration composition, wherein the hydrophilic biocompatible polymer may be 100-50,000 g/mol.

In addition, the present invention provides a tissue restoration composition, wherein the hydrophobic biocompatible polymer may be 500-70,000 g/mol.

Furthermore, the present invention provides a tissue restoration composition, wherein the copolymer may be 600-120,000 g/mol.

Moreover, the present invention provides a tissue restoration composition, wherein the concentration of the copolymer in a colloidal solution may be 10-50 wt %.

The present invention may provide a tissue restoration composition in a colloidal phase, including a copolymer in which a hydrophobic biocompatible polymer and a hydrophilic biocompatible polymer are polymerized, the tissue restoration composition being non-toxic and safe when the composition is injected in the living body, and being capable of applying to emergency patients.

DETAILED DESCRIPTION

Hereinafter, the present invention will be described in detail with reference to the exemplary embodiments. All terms or words used in the specification and claims should not be construed as a general or dictionary definition but are to be construed meaning and concepts meeting the technical spirits of the present invention based on a principle that the inventors can appropriately define the concepts of terms in order to describe their own inventions in best mode. Therefore, configurations described in embodiments of the present specification indicate only the most preferred example rather than indicating all the technical spirits of the present invention, and thus, it is to be understood that various equivalents and modifications that can replace the above configurations may be present. Further, throughout the specification, unless explicitly described to the contrary, the word "comprise", "include", "comprising", and/or "including" will be understood to imply the inclusion of stated elements but not the exclusion of any other elements.

The present inventors studied a biocompatible polymer to make a non-toxic, safe composition for tissue repair treatment which is capable of applying to emergency patients and being manufactured relatively inexpensively. As a result, it was observed that a copolymer in which a hydrophobic biocompatible polymer and a hydrophilic biocompatible polymer are polymerized can repair tissue safely without toxicity in vivo and apply to emergency patients, and the present invention was achieved.

Therefore, the present invention discloses a tissue restoration composition including a copolymer in which a hydrophobic biocompatible polymer and a hydrophilic biocompatible polymer are polymerized, and having a colloidal phase in which the copolymer is dispersed in water.

Figure 1:
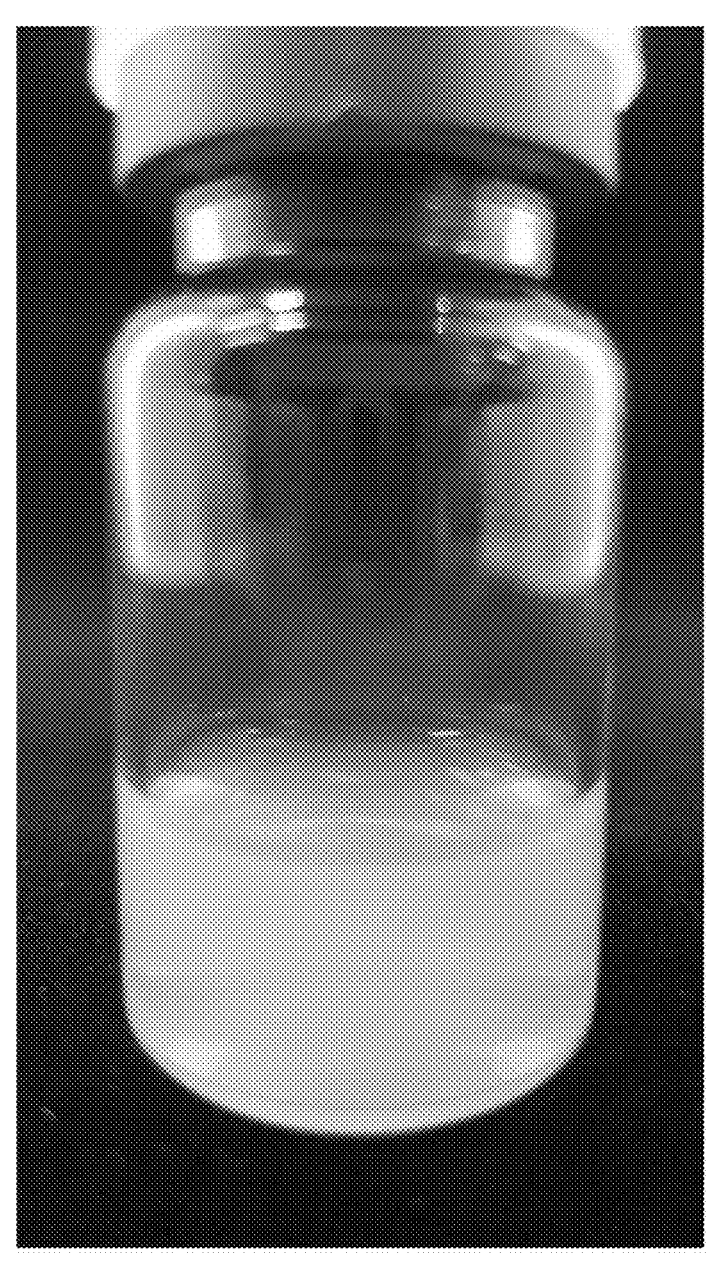
FIG. 1 is a picture taken with DSLR (D3000, Nikon, Japan), which shows a colloidal aqueous solution according to the present invention.

FIG. 1 is a picture taken of a colloidal aqueous solution according to the present invention.

The term "colloidal phase" refers to a state in which fine particles larger than molecules or ions are dispersed in gas or liquid, and the term "colloid" refers to the whole that is in a colloidal phase.

Particle size of the existing filler products can be identified with the naked eye, but the particle size of the colloidal phase according to the present invention cannot be identified with the naked eye, and insoluble foreign substance does not present in the colloid. The insoluble foreign substance refers to insoluble foreign substance which is easily detected when a solution formulation is added to a container which is cleaned according to Insoluble Particulate Matter Test, General Tests of United States Pharmacopeia (USP), and is then observed with the naked eye in the position of a brightness of about 2750-3000 lx directly below a white light source.

In the present invention, the particle size cannot be identified with the naked eye, and when the composition is injected into the body, polymers are bonded to each other to form a matrix structure, thereby exhibiting a long-lasting effect of tissue repair treatment in the skin without phagocytosis.

In the present invention, the colloidal phase may be heated to have an increase in the viscosity. Specifically, the colloidal phase is heated at a temperature from the melting point of the copolymer to the boiling point of water, thereby forming a colloid having improved viscosity. Generally, the colloidal phase in which the copolymer is dispersed in water is a state in which the copolymer is simply dispersed in water so that a composition is not formed and thus the viscosity is very low. However, the colloidal phase according to the present invention can be prepared as a composition by causing a reaction between the copolymers through various formulation methods such as dispersing the copolymer in water and then adding a small amount of an organic solvent, and preferably, a reaction can be caused by heating.

In addition, the copolymers react with each other by heat and thus the particle size cannot be identified with the naked eye, the insoluble foreign substance does not exist, the viscosity of the colloidal phase is increased as compared with that before the reaction occurs, and the increased viscosity is not lowered even when the temperature decreases.

In addition, the viscosity of the colloidal phase increased by causing a reaction between copolymers through the preparation method in the present invention may be 20-200,000 cP (centipoise), and preferably 25-190,000 cP (centipoise).

The range of K factor represented by the following equation 1 of the composition according to the present invention may be 0.01-5, preferably 0.3-1.8, and more preferably 0.4-1.5. If the K factor is less than 0.01 or greater than 5, the efficacy as a formulation may be decreased.

$$K=(m_{100}*M_h^2*10)/(M_1*HLB^2) \qquad \text{<Equation 1>}$$

In equation 1, $m_{100}$ is the number of moles of polymers in aqueous solution 100 g, $M_h$ is the molecular weight of a hydrophilic part, $M_1$ is the molecular weight of a hydrophobic part, and HLB is represented by the following equation 2, $$HLB=20*M_h/M \qquad \text{<Equation 2>}$$

In equation 2, $M_h$ is the molecular weight of the hydrophilic part, and M is the total molecular weight.

In a colloidal aqueous solution in which a copolymer in which a hydrophobic biocompatible polymer and a hydrophilic biocompatible polymer are polymerized is dissolved in water, the number of moles of the copolymer dissolved in 100 g of the aqueous solution has a value varying with the molecular weight of the hydrophilic biocompatible polymer, the molecular weight of the hydrophobic biocompatible polymer, and the mixture ratio, and thus the range of the tissue repair treatment effect of the composition for tissue repair treatment according to the present invention could not be set. In the present invention, to derive the range of the tissue repair treatment effect of the composition for tissue repair treatment, in a colloidal aqueous solution in which the copolymer in which a hydrophobic biocompatible polymer and a hydrophilic biocompatible polymer are polymerized is dissolved in water, the correlation among the number of moles of the copolymer dissolved in 100 g of the aqueous solution, the hydrophilic biocompatible polymer, the hydrophobic biocompatible polymer, and HLB is studied. As a result, a constant value is identified and is defined as K factor.

In other words, the K factor of the present invention represents the correlation among the number of moles of the copolymer dissolved in 100 g of the aqueous solution, the molecular weight of the hydrophilic biocompatible polymer, the molecular weight of the hydrophobic biocompatible polymer, and HLB value in a colloidal phase in which a copolymer in which a hydrophobic biocompatible polymer and a hydrophilic biocompatible polymer are polymerized is dispersed.

The K factor in the colloidal phase represents a constant value according to the number of moles of the copolymer dissolved in 100 g of the aqueous solution, the molecular weight of the hydrophilic biocompatible polymer, the molecular weight of the hydrophobic biocompatible polymer, and the HLB.

The efficacy of a formulation means that, before injection into the body, a hydrophilic polymer in a copolymer plays a major role, without insoluble foreign substance which can be identified with the naked eye due to the interaction of a solvent and a polymer, to form a colloidal phase in which polymers are uniformly and stably dispersed in an aqueous solution, but, after injection into the body, a hydrophobic polymer plays a major role, due to the influence of the environment in the body, to collapse the structure in which the polymers are stably dispersed in the aqueous solution, and then a matrix structure formed by bonding polymers to each other induces collagen, thereby repairing tissue.

Further, the repairing tissue refers to a mechanism that, when necrosis and loss occur in a tissue due to trauma or inflammation of a skin tissue, etc., restores the tissue to the original state.

The molecular weight of a polymer in the present invention refers to number average molecular weight (Mn). The number average molecular weight means an average molecular weight obtained by averaging the molecular weight of the component molecules of a polymer compound having a molecular weight distribution by number fraction or mole fraction.

HLB value by the equation 2 may be in a range of 0.1-20, preferably 1-14, more preferably 2-12, and still more preferably 2.5-10. If HLB value is less than 0.1, the polymerized copolymer may not be dissolved in water, and if HLB value is greater than 20, the composition is absorbed in the body during the injection of the composition into the body, so that the effect as a formulation cannot be exhibited.

The term "Hydrophile-Lipophile Balance (HLB) value" refers to an affinity for water and oil of an amphiphilic polymer. Large HLB indicates a high proportion of a hydrophilic polymer, and small HLB indicates a low proportion of a hydrophilic polymer.

In order to satisfy the K factor according to the equation 1, the hydrophobic biocompatible polymer may be at least any one polymer selected from the group consisting of polyglycolic acid, polycaprolactone, poly lactic acid, polydioxanone, poly(trimethylene carbonate), polyhydroxybutyrate, and a copolymer including the same, and preferably the hydrophobic biocompatible polymer may be polycaprolactone.

In order to satisfy the K factor according to the equation 1, the hydrophilic biocompatible polymer may be at least any one polymer selected from the group consisting of methoxy polyethylene glycol, dihydroxy polyethylene glycol, mono-alkoxy polyethylene glycol, and polyethylene glycol, and preferably, the hydrophilic biocompatible polymer may be methoxy polyethylene glycol.

The bonding structure of the copolymer may be, but is not limited to, represented by the structure of the following formula 1, formula 2, or formula 3:

$$X—Y \qquad \text{[Formula 1]}$$

$$Y—X—Y \qquad \text{[Formula 2]}$$

$$X—Y—X \qquad \text{[Formula 3]}$$

In formulae 1-3, X is a hydrophilic biocompatible polymer, and Y is a hydrophobic biocompatible polymer.

In order to satisfy the K factor according to the equation 1, the molecular weight of the hydrophilic biocompatible polymer may be 100-50,000 g/mol, preferably 300-20,000 g/mol, more preferably 700-15,000 g/mol, and still more preferably 1,000-10,000 g/mol.

In order to satisfy the K factor according to the equation 1, the molecular weight of the hydrophobic biocompatible polymer may be 500-70,000 g/mol, preferably 1,000-30,000 g/mol, more preferably 1,500-27,500 g/mol, and still more preferably 2,000-25,000 g/mol.

In order to satisfy the K factor according to the equation 1, the molecular weight of the copolymer may be 600-120,000 g/mol, preferably 1,300-50,000 g/mol, more preferably 2,200-42,500 g/mol, and still more preferably 3,000-35,000 g/mol.

In order to satisfy the K factor according to the equation 1, the concentration of the copolymer in the colloidal solution may be 10-50 wt %. If the concentration is more than 50 wt %, the colloidal aqueous solution becomes a gel phase having a very high viscosity, and thus it is very hard to be injected through a syringe, and if the concentration is less than 10 wt %, the effect as a formulation cannot be exhibited.

The colloidal phase has no changes or an increase in turbidity when water is added. A general colloidal phase has a decrease in turbidity when water is added, but the turbidity of the colloidal phase in the present invention does not decrease. The polymer dispersed in the colloidal phase in the present invention forms a structure in which a hydrophilic biopolymer and a hydrophobic biopolymer can be dissolved together in water. When water is added, however, a soluble structure formed by a hydrophilic biopolymer and a hydrophobic biopolymer is collapsed. Therefore, when water is added as above, bonding between hydrophobic biopolymers is formed, so that the turbidity of the colloidal phase does not change or rather increase.

Another aspect of the present invention provides a method for manufacturing the tissue restoration composition.

The method includes preparing a copolymer by polymerizing a hydrophobic biocompatible polymer and a hydrophilic biocompatible polymer, and obtaining a colloidal solution by adding the copolymer to water.

In this case, a colloidal solution, in which the copolymer is dispersed in water, is heated at a temperature between the melting point of the copolymer and the boiling point of water to form a phase of which the viscosity is increased, and further, to form a colloidal phase in which the particle size cannot be identified with the naked eye and insoluble foreign substance does not present.

When the tissue restoration composition manufactured by the method is injected into the skin, the composition exhibits effects of restoring a tissue forming collagen.

Hereinafter, the present invention is set forth with specific preparation examples and examples. Abbreviations for compounds used in the description of preparation examples and examples are the following:

mPEG: methoxy polyethylene glycol

PCL: polycaprolactone

Preparation Example 1: Preparation of
mPEG2000-PCL2000 Polymer Formulation

A copolymer (mPEG2000-PCL2000) was prepared by polymerizing methoxy polyethylene glycol, having a molecular weight of 2,000 g/mol, as a hydrophilic biocompatible polymer and polycaprolactone monomer, having a molecular weight of 2,000 g/mol, as a hydrophobic biocompatible polymer in the presence of a catalyst.

Preparation Example 2: Preparation of
mPEG2000-PCL4000 Polymer Formulation

Preparation Example 2 was prepared using the same method as Preparation Example 1, except that polymerization was performed by using polycaprolactone having a molecular weight of 4,000 g/mol instead of polycaprolactone having a molecular weight of 2,000 g/mol, in Preparation Example 1.

Preparation Example 3: Preparation of
mPEG2000-PCL5000 Polymer Formulation

Preparation Example 3 was prepared using the same method as Preparation Example 1, except that polymerization was performed by using polycaprolactone having a molecular weight of 5,000 g/mol instead of polycaprolactone having a molecular weight of 2,000 g/mol, in Preparation Example 1.

Preparation Example 4: Preparation of
mPEG2000-PCL7500 Polymer Formulation

Preparation Example 4 was prepared using the same method as Preparation Example 1, except that polymerization was performed by using polycaprolactone having a molecular weight of 7,500 g/mol instead of polycaprolactone having a molecular weight of 2,000 g/mol, in Preparation Example 1.

Preparation Example 5: Preparation of
mPEG2000-PCL10000 Polymer Formulation

Preparation Example 5 was prepared using the same method as Preparation Example 1, except that polymerization was performed by using polycaprolactone having a molecular weight of 10,000 g/mol instead of polycaprolactone having a molecular weight of 2,000 g/mol, in Preparation Example 1.

Preparation Example 6: Preparation of
mPEG2000-PCL12500 Polymer Formulation

Preparation Example 6 was prepared using the same method as Preparation Example 1, except that polymerization was performed by using polycaprolactone having a molecular weight of 12,500 g/mol instead of polycaprolactone having a molecular weight of 2,000 g/mol, in Preparation Example 1.

Preparation Example 7: Preparation of
mPEG2000-PCL15000 Polymer Formulation

Preparation Example 7 was prepared using the same method as Preparation Example 1, except that polymerization was performed by using polycaprolactone having a molecular weight of 15,000 g/mol instead of polycaprolactone having a molecular weight of 2,000 g/mol, in Preparation Example 1.

Preparation Example 8: Preparation of
mPEG5000-PCL5000 Polymer Formulation

A copolymer (mPEG5000-PCL5000) was prepared by polymerizing methoxy polyethylene glycol having a molecular weight of 5,000 g/mol as a hydrophilic biocompatible polymer and polycaprolactone monomer having a molecular weight of 5,000 g/mol as a hydrophobic biocompatible polymer in the presence of a catalyst.

Preparation Example 9: Preparation of mPEG5000-PCL7500 Polymer Formulation

Preparation Example 9 was prepared using the same method as Preparation Example 8, except that polymerization was performed by using polycaprolactone having a molecular weight of 7,500 g/mol instead of polycaprolactone having a molecular weight of 5,000 g/mol, in Preparation Example 8.

Preparation Example 10: Preparation of mPEG5000-PCL10000 Polymer Formulation Preparation Example 10 was prepared using the same method as Preparation Example 8, except that polymerization was performed by using polycaprolactone having a molecular weight of 10,000 g/mol instead of polycaprolactone having a molecular weight of 5,000 g/mol, in Preparation Example 8.

Preparation Example 11: Preparation of mPEG5000-PCL12500 Polymer Formulation Preparation Example 11 was prepared using the same method as Preparation Example 8, except that polymerization was performed by using polycaprolactone having a molecular weight of 12,500 g/mol instead of polycaprolactone having a molecular weight of 5,000 g/mol, in Preparation Example 8.

Preparation Example 12: Preparation of mPEG5000-PCL15000 Polymer Formulation Preparation Example 12 was prepared using the same method as Preparation Example 8, except that polymerization was performed by using polycaprolactone having a molecular weight of 15,000 g/mol instead of polycaprolactone having a molecular weight of 5,000 g/mol, in Preparation Example 8.

Preparation Example 13: Preparation of mPEG5000-PCL17500 Polymer Formulation Preparation Example 13 was prepared using the same method as Preparation Example 8, except that polymerization was performed by using polycaprolactone having a molecular weight of 17,500 g/mol instead of polycaprolactone having a molecular weight of 5,000 g/mol, in Preparation Example 8.

Preparation Example 14: Preparation of mPEG5000-PCL20000 Polymer Formulation Preparation Example 14 was prepared using the same method as Preparation Example 8, except that polymerization was performed by using polycaprolactone having a molecular weight of 20,000 g/mol instead of polycaprolactone having a molecular weight of 5,000 g/mol, in Preparation Example 8.

Preparation Example 15: Preparation of mPEG5000-PCL25000 Polymer Formulation Preparation Example 15 was prepared using the same method as Preparation Example 8, except that polymerization was performed by using polycaprolactone having a molecular weight of 25,000 g/mol instead of polycaprolactone having a molecular weight of 5,000 g/mol, in Preparation Example 8.

Preparation Example 16: Preparation of mPEG10000-PCL10000 Polymer Formulation A copolymer (mPEG10000-PCL10000) was prepared by polymerizing methoxy polyethylene glycol having a molecular weight of 10,000 g/mol as a hydrophilic biocompatible polymer and polycaprolactone monomer having a molecular weight of 10,000 g/mol as a hydrophobic biocompatible polymer in the presence of a catalyst.

Preparation Example 17: Preparation of mPEG10000-PCL12500 Polymer Formulation Preparation Example 17 was prepared using the same method as Preparation Example 16, except that polymerization was performed by using polycaprolactone having a molecular weight of 12,500 g/mol instead of polycaprolactone having a molecular weight of 10,000 g/mol, in Preparation Example 16.

Preparation Example 18: Preparation of mPEG10000-PCL15000 Polymer Formulation Preparation Example 18 was prepared using the same method as Preparation Example 16, except that polymerization was performed by using polycaprolactone having a molecular weight of 15,000 g/mol instead of polycaprolactone having a molecular weight of 10,000 g/mol, in Preparation Example 16.

Preparation Example 19: Preparation of mPEG10000-PCL17500 Polymer Formulation Preparation Example 19 was prepared using the same method as Preparation Example 16, except that polymerization was performed by using polycaprolactone having a molecular weight of 17,500 g/mol instead of polycaprolactone having a molecular weight of 10,000 g/mol, in Preparation Example 16.

Preparation Example 20: Preparation of mPEG10000-PCL20000 Polymer Formulation Preparation Example 20 was prepared using the same method as Preparation Example 16, except that polymerization was performed by using polycaprolactone having a molecular weight of 20,000 g/mol instead of polycaprolactone having a molecular weight of 10,000 g/mol, in Preparation Example 16.

Preparation Example 21: Preparation of mPEG10000-PCL25000 Polymer Formulation Preparation Example 21 was prepared using the same method as Preparation Example 16, except that polymerization was performed by using polycaprolactone having a molecular weight of 25,000 g/mol instead of polycaprolactone having a molecular weight of 10,000 g/mol, in Preparation Example 16.

Preparation Example 22: Preparation of mPEG10000-PCL30000 Polymer Formulation Preparation Example 22 was prepared using the same method as Preparation Example 16, except that polymerization was performed by using polycaprolactone having a molecular weight of 30,000 g/mol instead of polycaprolactone having a molecular weight of 10,000 g/mol, in Preparation Example 16.

Example 1

A colloidal aqueous solution having 5 wt % polymer was prepared by adding water to a polymer prepared by the Preparation Examples 1-22, heating to 80° C., and mixing.

Example 2

A colloidal aqueous solution was prepared using the same method as Example 1, except that a colloidal aqueous solution having 10 wt % polymer was prepared.

Example 3

A colloidal aqueous solution was prepared using the same method as Example 1, except that a colloidal aqueous solution having 15 wt % polymer was prepared.

Example 4

A colloidal aqueous solution was prepared using the same method as Example 1, except that a colloidal aqueous solution having 20 wt % polymer was prepared.

Example 5

A colloidal aqueous solution was prepared using the same method as Example 1, except that a colloidal aqueous solution having 25 wt % polymer was prepared.

Example 6

A colloidal aqueous solution was prepared using the same method as Example 1, except that a colloidal aqueous solution having 30 wt % polymer was prepared.

Example 7

A colloidal aqueous solution was prepared using the same method as Example 1, except that a colloidal aqueous solution having 35 wt % polymer was prepared.

Example 8

A colloidal aqueous solution was prepared using the same method as Example 1, except that a colloidal aqueous solution having 40 wt % polymer was prepared.

Example 9

A colloidal aqueous solution was prepared using the same method as Example 1, except that a colloidal aqueous solution having 45 wt % polymer was prepared.

Example 10

A colloidal aqueous solution was prepared using the same method as Example 1, except that a colloidal aqueous solution having 50 wt % polymer was prepared.

Example 11

A colloidal aqueous solution was prepared using the same method as Example 1, except that a colloidal aqueous solution having 55 wt % polymer was prepared.

Example 12

A colloidal aqueous solution was prepared using the same method as Example 1, except that a colloidal aqueous solution having 60 wt % polymer was prepared.

Example 13

A colloidal aqueous solution was prepared using the same method as Example 1, except that a colloidal aqueous solution having 65 wt % polymer was prepared.

Comparative Example

A mixture having 15 wt % polymer was prepared by adding water to a polymer prepared by the Preparation Example 5, and mixing.

Experimental Example 1

The number of moles of a polymer in 100 g of an aqueous solution for the tissue restoration compositions prepared according to the Examples 1-13 was measured, and the K factor according to the following equation 1 was measured. The effect of a formulation was evaluated according to this, the results are shown in Tables 1 and 2 below (the part of the efficacy of a formulation is indicated in bold).

$$K=(m_{100}*M_h^2*10)/(M_1*HLB^2) \qquad \text{<Equation 1>}$$

In equation 1, $m_{100}$ is the number of moles of polymers in 100 g of aqueous solution, $M_h$ is the molecular weight of a hydrophilic part, $M_1$ is the molecular weight of a hydrophobic part, and HLB is represented by the following equation 2, $$HLB=20*M_h/M \qquad \text{<Equation 2>}$$

In equation 2, $M_h$ is the molecular weight of the hydrophilic part, and M is the total molecular weight.

TABLE 1

| | Concentration of polymer in Aqueous solution (wt %) | | | | | | | | | |
| | mPEG | PCL | HLB | 5% | 10% | 15% | 20% | 25% | 30% | 35% |
|---|---|---|---|---|---|---|---|---|---|---|
| Number | 2000 | 2000 | 10.00 | 0.0013 | 0.0025 | 0.0038 | 0.0050 | 0.0063 | 0.0075 | 0.0088 |
| of moles | 2000 | 4000 | 6.67 | 0.0008 | 0.0017 | 0.0025 | 0.0033 | 0.0042 | 0.0050 | 0.0058 |
| of | 2000 | 5000 | 5.71 | 0.0007 | 0.0014 | 0.0021 | 0.0029 | 0.0036 | 0.0043 | 0.0050 |
| polymer | 2000 | 7500 | 4.21 | 0.0005 | 0.0011 | 0.0016 | 0.0021 | 0.0026 | 0.0032 | 0.0037 |
| in 100 g | 2000 | 10000 | 3.33 | 0.0004 | 0.0008 | 0.0013 | 0.0017 | 0.0021 | 0.0025 | 0.0029 |
| of | 2000 | 12500 | 2.76 | 0.0003 | 0.0007 | 0.0010 | 0.0014 | 0.0017 | 0.0021 | 0.0024 |
| Aqueous | 2000 | 15000 | 2.35 | 0.0003 | 0.0006 | 0.0009 | 0.0012 | 0.0015 | 0.0018 | 0.0021 |
| solution | 5000 | 5000 | 10.00 | 0.0005 | 0.0010 | 0.0015 | 0.0020 | 0.0025 | 0.0030 | 0.0035 |

TABLE 1-continued

| | | HLB | | | | | | | |
|---|---|---|---|---|---|---|---|---|---|
| 5000 | 7500 | 8.00 | 0.0004 | 0.0008 | 0.0012 | 0.0016 | 0.0020 | 0.0024 | 0.0028 |
| 5000 | 10000 | 6.67 | 0.0003 | 0.0007 | 0.0010 | 0.0013 | 0.0017 | 0.0020 | 0.0023 |
| 5000 | 12500 | 5.71 | 0.0003 | 0.0006 | 0.0009 | 0.0011 | 0.0014 | 0.0017 | 0.0020 |
| 5000 | 15000 | 5.00 | 0.0003 | 0.0005 | 0.0008 | 0.0010 | 0.0013 | 0.0015 | 0.0018 |
| 5000 | 17500 | 4.44 | 0.0002 | 0.0004 | 0.0007 | 0.0009 | 0.0011 | 0.0013 | 0.0016 |
| 5000 | 20000 | 4.00 | 0.0002 | 0.0004 | 0.0006 | 0.0008 | 0.0010 | 0.0012 | 0.0014 |
| 5000 | 25000 | 3.33 | 0.0002 | 0.0003 | 0.0005 | 0.0007 | 0.0008 | 0.0010 | 0.0012 |
| 10000 | 10000 | 10.00 | 0.0003 | 0.0005 | 0.0008 | 0.0010 | 0.0013 | 0.0015 | 0.0018 |
| 10000 | 12500 | 8.89 | 0.0002 | 0.0004 | 0.0007 | 0.0009 | 0.0011 | 0.0013 | 0.0016 |
| 10000 | 15000 | 8.00 | 0.0002 | 0.0004 | 0.0006 | 0.0008 | 0.0010 | 0.0012 | 0.0014 |
| 10000 | 17500 | 7.27 | 0.0002 | 0.0004 | 0.0005 | 0.0007 | 0.0009 | 0.0011 | 0.0013 |
| 10000 | 20000 | 6.67 | 0.0002 | 0.0003 | 0.0005 | 0.0007 | 0.0008 | 0.0010 | 0.0012 |
| 10000 | 25000 | 5.71 | 0.0001 | 0.0003 | 0.0004 | 0.0006 | 0.0007 | 0.0009 | 0.0010 |
| 10000 | 30000 | 5.00 | 0.0001 | 0.0003 | 0.0004 | 0.0005 | 0.0006 | 0.0008 | 0.0009 |

| | | | | Concentration of polymer in Aqueous solution (wt %) | | | | | |
|---|---|---|---|---|---|---|---|---|---|
| | mPEG | PCL | HLB | 40% | 45% | 50% | 55% | 60% | 65% |
| Number | 2000 | 2000 | 10.00 | 0.0100 | 0.0113 | 0.0125 | 0.0138 | 0.0150 | 0.0163 |
| of moles | 2000 | 4000 | 6.67 | 0.0067 | 0.0075 | 0.0083 | 0.0092 | 0.0100 | 0.0108 |
| of | | | | | | | | | |
| polymer | 2000 | 5000 | 5.71 | 0.0057 | 0.0064 | 0.0071 | 0.0079 | 0.0086 | 0.0093 |
| in 100 g | 2000 | 7500 | 4.21 | 0.0042 | 0.0047 | 0.0053 | 0.0058 | 0.0063 | 0.0068 |
| of | 2000 | 10000 | 3.33 | 0.0033 | 0.0038 | 0.0042 | 0.0046 | 0.0050 | 0.0054 |
| Aqueous | 2000 | 12500 | 2.76 | 0.0028 | 0.0031 | 0.0034 | 0.0038 | 0.0041 | 0.0045 |
| solution | 2000 | 15000 | 2.35 | 0.0024 | 0.0026 | 0.0029 | 0.0032 | 0.0035 | 0.0038 |
| | 5000 | 5000 | 10.00 | 0.0040 | 0.0045 | 0.0050 | 0.0055 | 0.0060 | 0.0065 |
| | 5000 | 7500 | 8.00 | 0.0032 | 0.0036 | 0.0040 | 0.0044 | 0.0048 | 0.0052 |
| | 5000 | 10000 | 6.67 | 0.0027 | 0.0030 | 0.0033 | 0.0037 | 0.0040 | 0.0043 |
| | 5000 | 12500 | 5.71 | 0.0023 | 0.0026 | 0.0029 | 0.0031 | 0.0034 | 0.0037 |
| | 5000 | 15000 | 5.00 | 0.0020 | 0.0023 | 0.0025 | 0.0028 | 0.0030 | 0.0033 |
| | 5000 | 17500 | 4.44 | 0.0018 | 0.0020 | 0.0022 | 0.0024 | 0.0027 | 0.0029 |
| | 5000 | 20000 | 4.00 | 0.0016 | 0.0018 | 0.0020 | 0.0022 | 0.0024 | 0.0026 |
| | 5000 | 25000 | 3.33 | 0.0013 | 0.0015 | 0.0017 | 0.0018 | 0.0020 | 0.0022 |
| | 10000 | 10000 | 10.00 | 0.0020 | 0.0023 | 0.0025 | 0.0028 | 0.0030 | 0.0033 |
| | 10000 | 12500 | 8.89 | 0.0018 | 0.0020 | 0.0022 | 0.0024 | 0.0027 | 0.0029 |
| | 10000 | 15000 | 8.00 | 0.0016 | 0.0018 | 0.0020 | 0.0022 | 0.0024 | 0.0026 |
| | 10000 | 17500 | 7.27 | 0.0015 | 0.0016 | 0.0018 | 0.0020 | 0.0022 | 0.0024 |
| | 10000 | 20000 | 6.67 | 0.0013 | 0.0015 | 0.0017 | 0.0018 | 0.0020 | 0.0022 |
| | 10000 | 25000 | 5.71 | 0.0011 | 0.0013 | 0.0014 | 0.0016 | 0.0017 | 0.0019 |
| | 10000 | 30000 | 5.00 | 0.0010 | 0.0011 | 0.0013 | 0.0014 | 0.0015 | 0.0016 |

TABLE 2

| | | | | Concentration of polymer in Aqueous solution (wt %) | | | | | | |
|---|---|---|---|---|---|---|---|---|---|---|
| | PEG | PCL | HLB | 5% | 10% | 15% | 20% | 25% | 30% | 35% |
| K | 2000 | 2000 | 10.00 | 0.2500 | 0.5000 | 0.7500 | 1.0000 | 1.2500 | 1.5000 | 1.7500 |
| factor | 2000 | 4000 | 6.67 | 0.1875 | 0.3750 | 0.5625 | 0.7500 | 0.9375 | 1.1250 | 1.3125 |
| | 2000 | 5000 | 5.71 | 0.1750 | 0.3500 | 0.5250 | 0.7000 | 0.8750 | 1.0500 | 1.2250 |
| | 2000 | 7500 | 4.21 | 0.1583 | 0.3167 | 0.4750 | 0.6333 | 0.7917 | 0.9500 | 1.1083 |
| | 2000 | 10000 | 3.33 | 0.1500 | 0.3000 | 0.4500 | 0.6000 | 0.7500 | 0.9000 | 1.0500 |
| | 2000 | 12500 | 2.76 | 0.1450 | 0.2900 | 0.4350 | 0.5800 | 0.7250 | 0.8700 | 1.0150 |
| | 2000 | 15000 | 2.35 | 0.1417 | 0.2833 | 0.4250 | 0.5667 | 0.7083 | 0.8500 | 0.9917 |
| | 5000 | 5000 | 10.00 | 0.2500 | 0.5000 | 0.7500 | 1.0000 | 1.2500 | 1.5000 | 1.7500 |
| | 5000 | 7500 | 8.00 | 0.2083 | 0.4167 | 0.6250 | 0.8333 | 1.0417 | 1.2500 | 1.4583 |
| | 5000 | 10000 | 6.67 | 0.1875 | 0.3750 | 0.5625 | 0.7500 | 0.9375 | 1.1250 | 1.3125 |
| | 5000 | 12500 | 5.71 | 0.1750 | 0.3500 | 0.5250 | 0.7000 | 0.8750 | 1.0500 | 1.2250 |
| | 5000 | 15000 | 5.00 | 0.1667 | 0.3333 | 0.5000 | 0.6667 | 0.8333 | 1.0000 | 1.1667 |
| | 5000 | 17500 | 4.44 | 0.1607 | 0.3214 | 0.4821 | 0.6429 | 0.8036 | 0.9643 | 1.1250 |
| | 5000 | 20000 | 4.00 | 0.1563 | 0.3125 | 0.4688 | 0.6250 | 0.7813 | 0.9375 | 1.0938 |
| | 5000 | 25000 | 3.33 | 0.1500 | 0.3000 | 0.4500 | 0.6000 | 0.7500 | 0.9000 | 1.0500 |
| | 10000 | 10000 | 10.00 | 0.2500 | 0.5000 | 0.7500 | 1.0000 | 1.2500 | 1.5000 | 1.7500 |
| | 10000 | 12500 | 8.89 | 0.2250 | 0.4500 | 0.6750 | 0.9000 | 1.1250 | 1.3500 | 1.5750 |
| | 10000 | 15000 | 8.00 | 0.2083 | 0.4167 | 0.6250 | 0.8333 | 1.0417 | 1.2500 | 1.4583 |
| | 10000 | 17500 | 7.27 | 0.1964 | 0.3929 | 0.5893 | 0.7857 | 0.9821 | 1.1786 | 1.3750 |
| | 10000 | 20000 | 6.67 | 0.1875 | 0.3750 | 0.5625 | 0.7500 | 0.9375 | 1.1250 | 1.3125 |
| | 10000 | 25000 | 5.71 | 0.1750 | 0.3500 | 0.5250 | 0.7000 | 0.8750 | 1.0500 | 1.2250 |
| | 10000 | 30000 | 5.00 | 0.1667 | 0.3333 | 0.5000 | 0.6667 | 0.8333 | 1.0000 | 1.1667 |

TABLE 2-continued

| | PEG | PCL | HLB | Concentration of polymer in Aqueous solution (wt %) | | | | | |
| | | | | 40% | 45% | 50% | 55% | 60% | 65% |
|---|---|---|---|---|---|---|---|---|---|
| K | 2000 | 2000 | 10.00 | 2.0000 | 2.2500 | 2.5000 | 2.7500 | 3.0000 | 3.2500 |
| factor | 2000 | 4000 | 6.67 | 1.5000 | 1.6875 | 1.8750 | 2.0625 | 2.2500 | 2.4375 |
| | 2000 | 5000 | 5.71 | 1.4000 | 1.5750 | 1.7500 | 1.9250 | 2.1000 | 2.2750 |
| | 2000 | 7500 | 4.21 | 1.2667 | 1.4250 | 1.5833 | 1.7417 | 1.9000 | 2.0583 |
| | 2000 | 10000 | 3.33 | 1.2000 | 1.3500 | 1.5000 | 1.6500 | 1.8000 | 1.9500 |
| | 2000 | 12500 | 2.76 | 1.1600 | 1.3050 | 1.4500 | 1.5950 | 1.7400 | 1.8850 |
| | 2000 | 15000 | 2.35 | 1.1333 | 1.2750 | 1.4167 | 1.5583 | 1.7000 | 1.8417 |
| | 5000 | 5000 | 10.00 | 2.0000 | 2.2500 | 2.5000 | 2.7500 | 3.0000 | 3.2500 |
| | 5000 | 7500 | 8.00 | 1.6667 | 1.8750 | 2.0833 | 2.2917 | 2.5000 | 2.7083 |
| | 5000 | 10000 | 6.67 | 1.5000 | 1.6875 | 1.8750 | 2.0625 | 2.2500 | 2.4375 |
| | 5000 | 12500 | 5.71 | 1.4000 | 1.5750 | 1.7500 | 1.9250 | 2.1000 | 2.2750 |
| | 5000 | 15000 | 5.00 | 1.3333 | 1.5000 | 1.6667 | 1.8333 | 2.0000 | 2.1667 |
| | 5000 | 17500 | 4.44 | 1.2857 | 1.4464 | 1.6071 | 1.7679 | 1.9286 | 2.0893 |
| | 5000 | 20000 | 4.00 | 1.2500 | 1.4063 | 1.5625 | 1.7188 | 1.8750 | 2.0313 |
| | 5000 | 25000 | 3.33 | 1.2000 | 1.3500 | 1.5000 | 1.6500 | 1.8000 | 1.9500 |
| | 10000 | 10000 | 10.00 | 2.0000 | 2.2500 | 2.5000 | 2.7500 | 3.0000 | 3.2500 |
| | 10000 | 12500 | 8.89 | 1.8000 | 2.0250 | 2.2500 | 2.4750 | 2.7000 | 2.9250 |
| | 10000 | 15000 | 8.00 | 1.6667 | 1.8750 | 2.0833 | 2.2917 | 2.5000 | 2.7083 |
| | 10000 | 17500 | 7.27 | 1.5714 | 1.7679 | 1.9643 | 2.1607 | 2.3571 | 2.5536 |
| | 10000 | 20000 | 6.67 | 1.5000 | 1.6875 | 1.8750 | 2.0625 | 2.2500 | 2.4375 |
| | 10000 | 25000 | 5.71 | 1.4000 | 1.5750 | 1.7500 | 1.9250 | 2.1000 | 2.2750 |
| | 10000 | 30000 | 5.00 | 1.3333 | 1.5000 | 1.6667 | 1.8333 | 2.0000 | 2.1667 |

Referring to Table 1, the number of moles of a polymer dissolved in 100 g of an aqueous solution can be seen, and it can be seen that the lower HLB value in a constant concentration, the fewer the number of moles.

When the concentration was more than 45 wt %, the viscosity of the colloidal aqueous solution was enhanced, so that it was hard to be injected through a syringe, and when the concentration was less than 15 wt %, the effect as a formulation was not exhibited.

Further, when HLB was less than 2.5, the rate of the hydrophobic biocompatible polymer was high, so that when water was added, the polymer was not dissolved, and when HLB was more than 10, the composition was absorbed in the body during the injection of the composition into the body, so that the effect as a formulation was not exhibited.

However, determining with not a proportion of a hydrophilic biopolymer and a hydrophobic biopolymer, but the molecular weight of a polymer polymerized in Table 1, comparing mPEG 2,000 g/mol and mPEG 5,000 g/mol, when mPEG was 2,000 g/mol, the number of moles of a polymer in 100 g of an aqueous solution increased more than when mPEG was 5,000 g/mol. Therefore, the number of moles of a polymer in 100 g of an aqueous solution was not constant, and thus converting this to a constant value, through this to measure a forming range of a tissue restoration composition according to the present invention, resulting in K factor.

Referring to Table 2, unlike Table 1, a relationship between the molecular weight of a hydrophilic biopolymer and a hydrophobic biopolymer and HLB value may be understood, when the molecular weight of a hydrophilic biopolymer is the same, the higher the molecular weight of a hydrophobic biopolymer, the lower the K factor. This is the same as determining with a proportion of a hydrophilic biopolymer and a hydrophobic biopolymer. Further, it can be seen that even though the molecular weight of a hydrophilic biopolymer is different, when a proportion of a hydrophilic biopolymer and a hydrophobic biopolymer is the same, the K factor has a very similar value.

The K factor has a constant value within a range of a certain concentration discussed below, the effect of a formulation within this range may be identified. In addition, the K factor is converted about 0.12-3.26, the part of the effect of a formulation is in a range of 0.4-1.5.

Furthermore, it may be identified that the effect as a formulation is in a concentration of 15-45 wt % in a colloidal aqueous solution, HLB of 2.5-10, and K factor of 0.4-1.5.

Experimental Example 2

Figure 9:
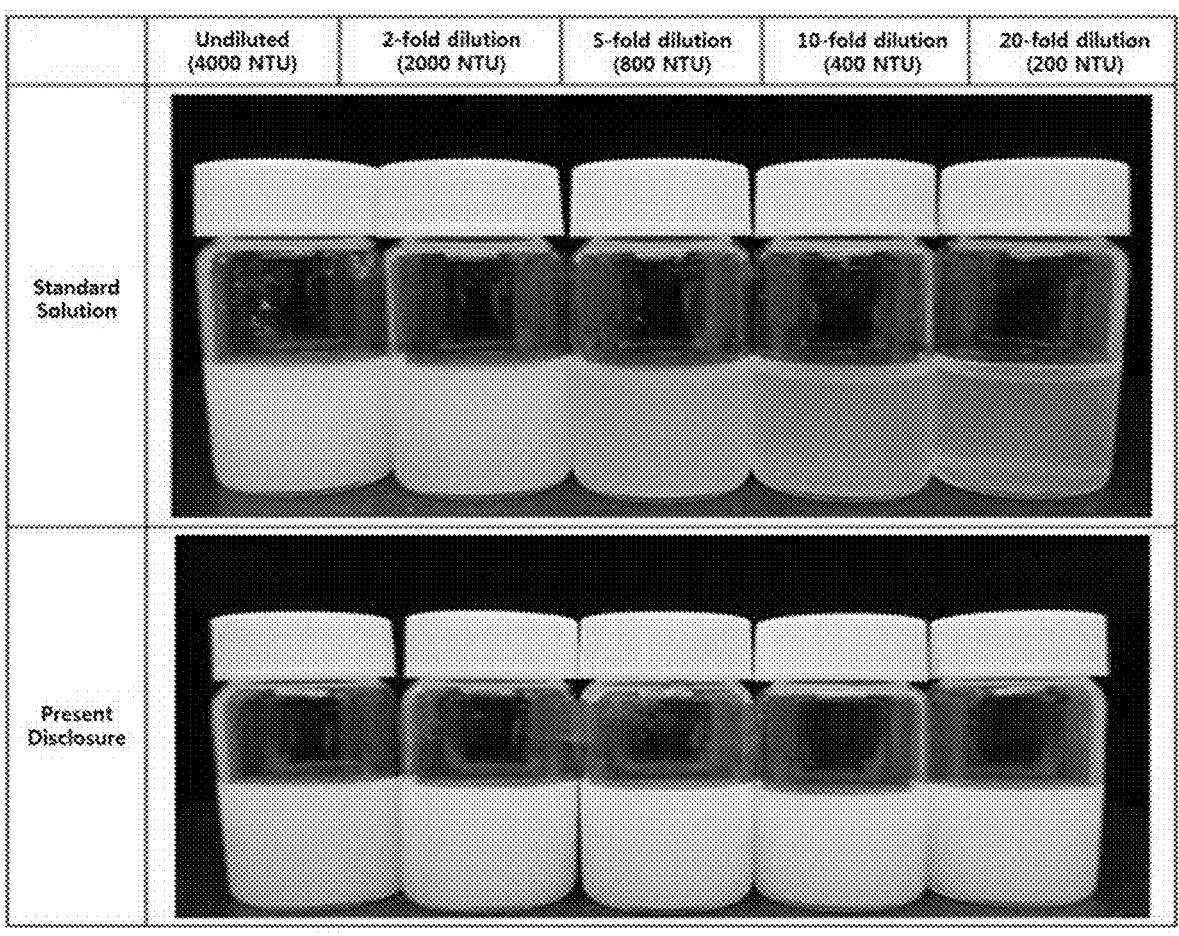
FIG. 9 illustrates results of comparative experiments for measuring a turbidity of a tissue restoration composition with a turbidity standard solution and a tissue restoration composition according to the present invention prepared using Preparation Example 3.

To measure a turbidity of a tissue restoration composition according to the present invention as the following method, a colloidal phase prepared using Preparation Example 3 was used, and the results are shown in FIG. 9. Formazin turbidity standard, 4000 NTU was used as a turbidity standard solution.

<Method of Measuring>

(1) Comparable samples were prepared by making solutions in which colloidal phases prepared using a standard solution and Preparation Example 3 were diluted 2-fold, 5-fold, 10-fold, and 20-fold, respectively, and putting each of the solutions in a vial, and the turbidities of the standard solutions diluted were 4,000, 2,000, 800, 400, and 200 NTU, respectively.

(2) After cleaning the outside of each vial of samples for comparing turbidity, changes in the turbidity due to dilution and difference of the turbidity in the same dilution rate were observed in a brightness of about 1000 lx below white LED light source.

Seeing FIG. 9, for the standard solution, from left to right, it can be seen that the more dilution the lower turbidity.

In contrast, for the present invention, from left to right, it can be identified with the naked eye that even though the solution was diluted, the turbidity did not decrease, and rather, the turbidity increased more than the undiluted solution.

Experimental Example 3

The viscosities of the colloidal aqueous solutions exhibiting the efficacy of a formulation in the colloidal aqueous solutions prepared according to Examples 1 to 13, and the

Figure 2:
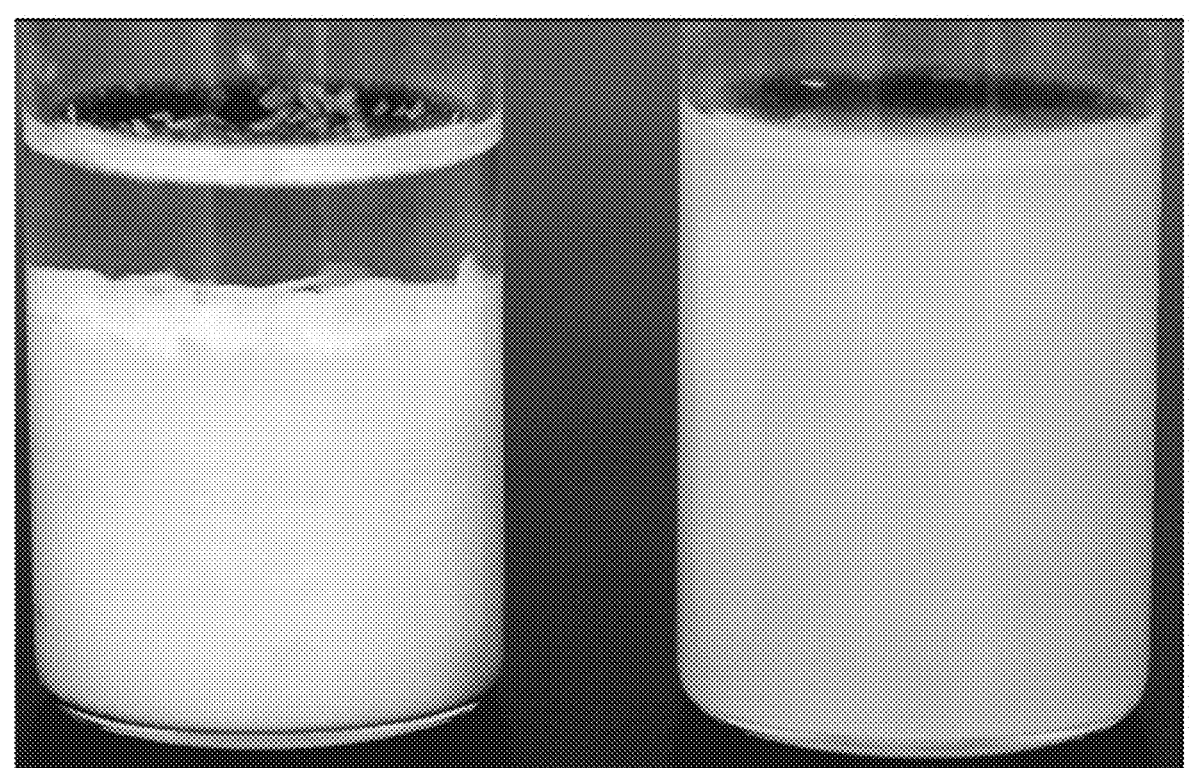
FIG. 2 is a picture taken with DSLR (D3000, Nikon, Japan), which shows results according to Experimental Example 3 of the present invention.

17 mixture prepared according to Comparative Example were measured by using a viscometer (Viscolead One, Fungilab) at room temperature, and the results are shown in Table 3 and FIG. 2 below. For Examples 1 to 13, the viscosities of the colloidal aqueous solutions using copolymers prepared according to Preparation Examples 1 to 8, 10, 11, 13, and 14 were measured. In FIG. 2, (b) shows the result of the colloidal aqueous solution of Example 3 using the copolymer prepared according to Preparation Example 5. The viscosity of the mixture prepared according to Comparative Example was 1.14 cP.

18

Immediately after administering the colloidal aqueous solution and PBS (0 hr), the experimental animals were sacrificed after one week, two weeks, four weeks, and six weeks, respectively, the skin tissues in which the samples were injected and the skin tissues in which the samples were not injected were harvested and fixed in 10% neutral buffered formalin solution. Then, the skin tissues were embedded in paraffin and solidified, and 5 $\mu$m sections were prepared. The sections were stained with Hematoxylin and Eosin (H&E), and inflammation/foreign substance reaction was then evaluated according to FIG. 9. Thickness increase

TABLE 3

| | Concentration of polymer in Aqueous solution (wt %) | | | | | | | | | | | | | | | |
| | PEG | PCL | HLB | 5% | 10% | 15% | 20% | 25% | 30% | 35% | 40% | 45% | 50% | 55% | 60% | 65% |
|---|---|---|---|---|---|---|---|---|---|---|---|---|---|---|---|---|
| Viscosity | 2000 | 2000 | 10.0 | | | 605.6 | 2002.8 | 26453.3 | | | | | | | | |
| | 2000 | 4000 | 6.7 | | | 55.3 | 87.3 | 208.1 | 758.3 | 1470.9 | | | | | | |
| | 2000 | 5000 | 5.7 | | | 45.1 | 70.4 | 155.4 | 529.3 | 982.6 | | | | | | |
| | 2000 | 7500 | 4.2 | | | 132.8 | 542.9 | 5943.9 | 6805.4 | 45526.4 | 188404.6 | | | | | |
| | 2000 | 10000 | 3.3 | | | 509.3 | 4171.0 | 4263.8 | 10186.0 | 29468.3 | 72545.7 | 178594.2 | | | | |
| | 2000 | 12500 | 2.8 | | | 83.7 | 264.1 | 544.8 | 1876.6 | 7551.3 | 18842.1 | 56409.7 | | | | |
| | 2000 | 15000 | 2.4 | | | | | | | | | | | | | |
| | 5000 | 5000 | 10.0 | | | 80.2 | 265.3 | 3503.7 | 18389.1 | | | | | | | |
| | 5000 | 10000 | 6.7 | | | | 111.4 | 259.2 | 1460.8 | 10063.1 | | | | | | |
| | 5000 | 12500 | 5.7 | | | | 103.7 | 185.9 | 448.2 | 1088.9 | | | | | | |
| | 5000 | 17500 | 4.4 | | | | 74.0 | 139.1 | 246.0 | 792.4 | | | | | | |
| | 5000 | 20000 | 4.0 | | | | 26.4 | 36.6 | 55.9 | 150.3 | | | | | | |
| | 5000 | 25000 | 3.3 | | | | | 30.2 | 40.3 | 72.2 | | | | | | |

Referring to FIG. 2, it may be confirmed that when compared with the unheated mixture (Comparative Example), the heated colloidal aqueous solution (Example 1) has no precipitation and foreign substances and an increase in the viscosity.

In addition, referring to Table 3, it may be confirmed that the viscosity of the heated colloidal aqueous solution has a tendency in that the higher the concentration of the polymer in the aqueous solution, the higher the viscosity in a range of 26.4 to 188404.6 cP, and it may be seen that the viscosity of the heated colloidal aqueous solution increases to a level of about 25-fold to about 190,000-fold over the unheated mixture (Comparative Example).

Experimental Example 4

To validate the efficacy as a formulation of the tissue restoration composition according to the present invention, animal experiments were performed.

Six week-old SD rats (purchased from Orient Bio) were used as an experimental animal.

The experiment was performed that the total 10 rats were subdivided into three groups by designating that one side is phosphate buffered saline (PBS) group, and the other is test sample group in eight sites per a six week-old SD rat individual. During experiment, feeding environment was set as a temperature of 24±2° C., a relative humidity of 50±10%, and a lighting time of 12 hours, and animals were allowed to eat feeds freely.

Figure 3:
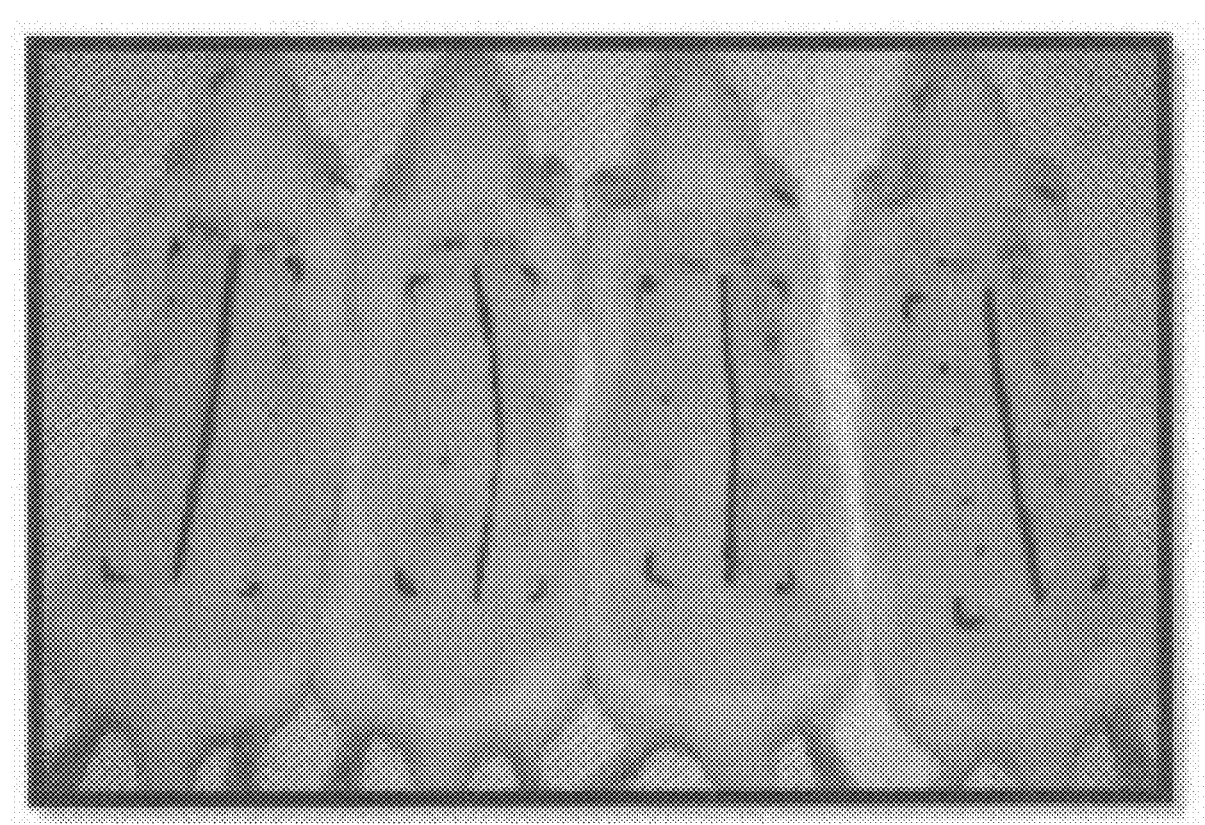
FIG. 3 is a picture which is taken with DSLR (D3000, Nikon, Japan) to confirm whether samples are leaked after PBS and a colloidal aqueous solution are injected.
Figure 4:
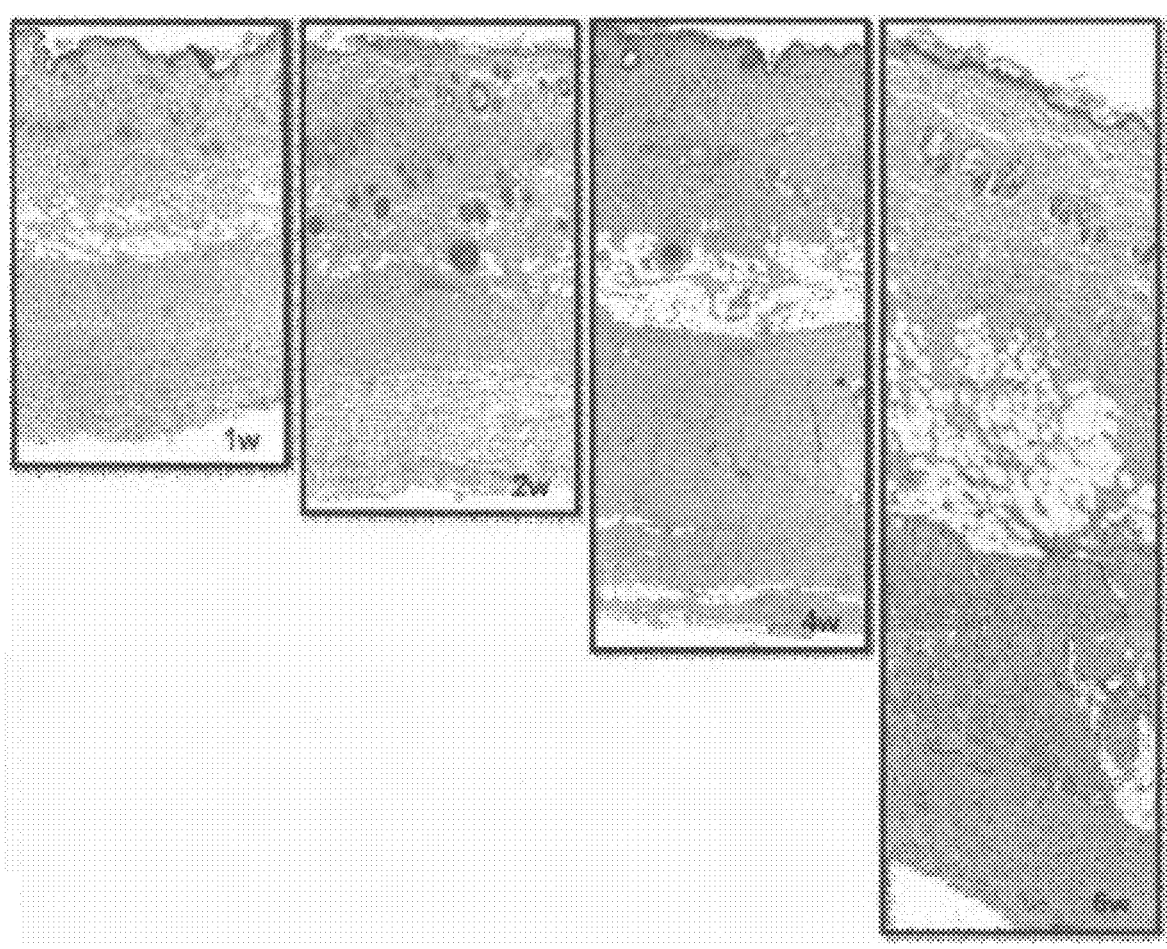
FIG. 4 is a picture, which is taken through an optical microscope, and shows a skin thickness over time after a colloidal aqueous solution is injected.
Figure 6:
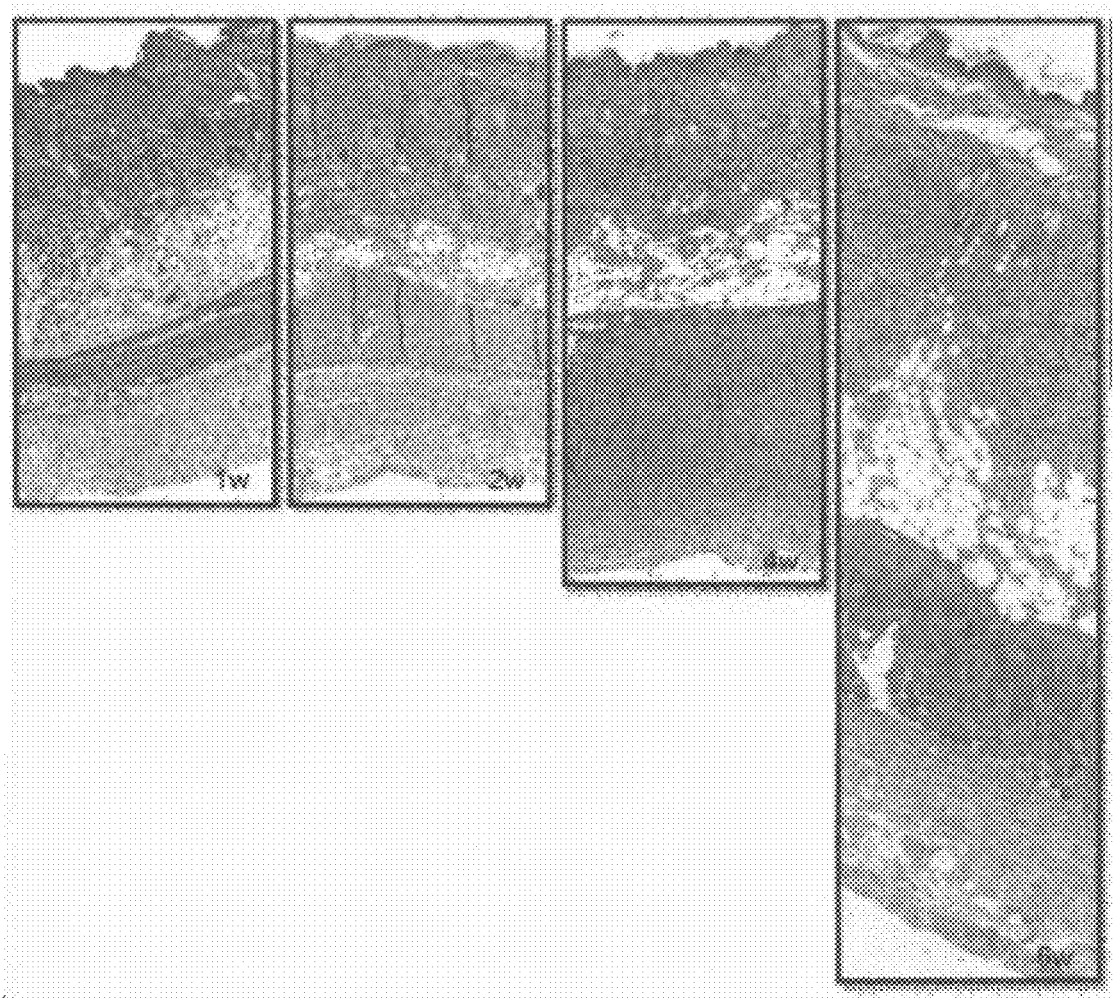
FIG. 6 is a picture, which is taken through an optical microscope, and shows a skin thickness over time after PBS is injected.
Figure 8:
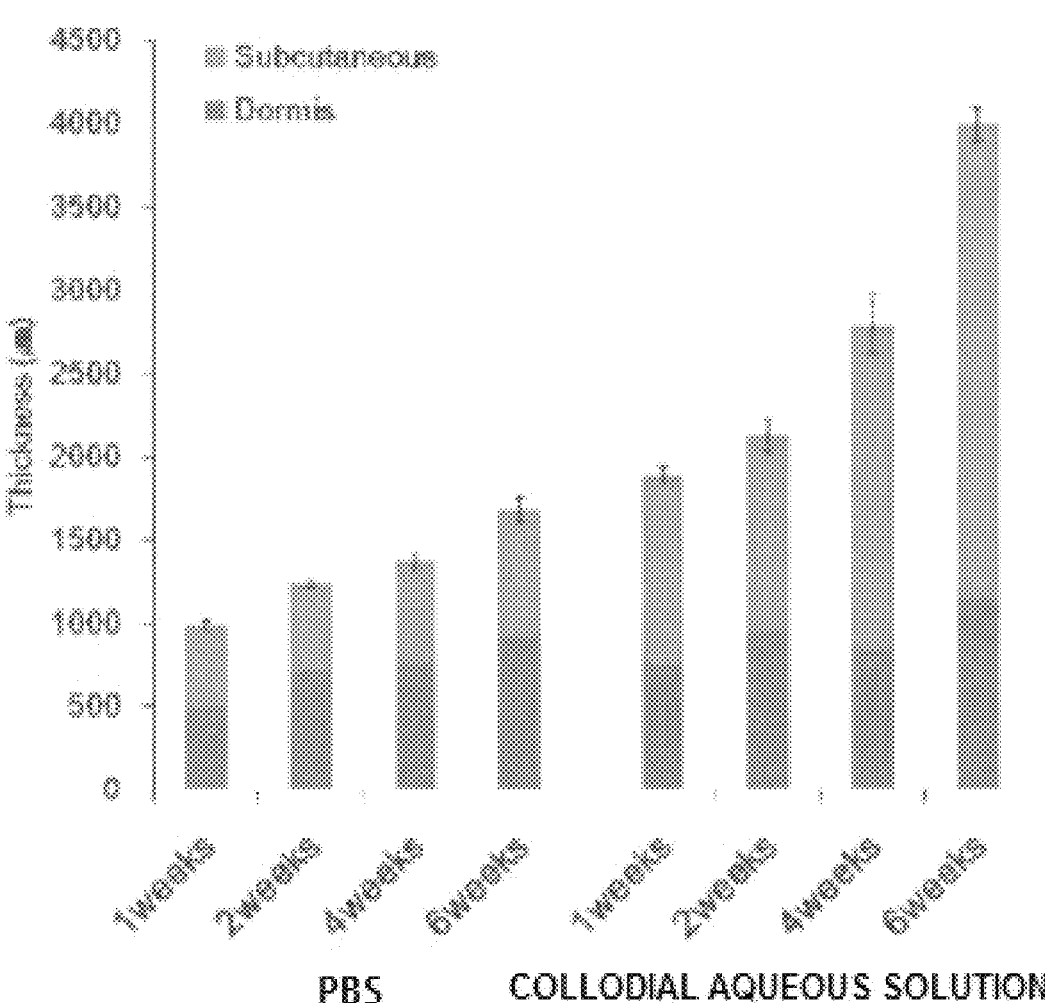
FIG. 8 is a graph showing a skin thickness over time after PBS and a colloidal aqueous solution are injected.

PBS was injected to the left subcutaneous layer with respect to the center line of a rat in each group, and a colloidal aqueous solution prepared by dissolving a polymer in water, which was prepared in the Preparation Example 3 (which has a concentration of 25%, HLB of 5.7, K factor of 0.8864) is regularly injected at 250 $\mu$L. Immediately after the injection, it was observed whether the samples were leaked, and the results are shown in FIG. 3.

of the whole skin layer (dermal layer and subcutaneous layer) due to the sample injection was observed through an optical microscope, and the results are shown in FIGS. 4, 6, and 8, respectively.

In addition, to evaluate a biosynthesis ability of new collagen of a colloidal aqueous solution and PBS, the sections were stained with Masson's Trichrome (MT), and collagen formation in the tissue was then observed. Histocompatibility of the samples injected was evaluated through confirming inflammation and foreign substance reaction according to Table 3 as major criteria. Tissue slides were observed with 40×, 100×, 200×, and 400× using an optical microscope, major histological features of each slide were deciphered, and the results were shown in FIGS. 5 and 7.

Further, the degree of inflammation and foreign substance reaction due to the colloidal aqueous solution injected is divided into four stages. Inflammation and foreign substance reaction which is observed in PBS-administered group is set as no inflammation, and as inflammation reaction or foreign substance reaction is intensified, the degree is set as almost clear (score 1), mild (score 2), moderate (score 3), severe (score 4) and evaluated according to Table 4 below (Duranti et al. Dermatol Surg 1998:24:1317-25).

TABLE 4

| | Grade | Foreign body granuloma |
|---|---|---|
| Score 0 | No inflammation | No visible reaction |
| Score 1 | Almost clear | Slight reaction with a few inflammatory cells |
| Score 2 | Mild | Clear inflammatory reaction with one or two giant cells |
| Score 3 | Moderate | Fibrous tissue with inflammatory cells, lymphocytes and giant cells |
| Score 4 | severe | Granuloma with encapsulated implant-clear foreign body reaction |

Figure 5:
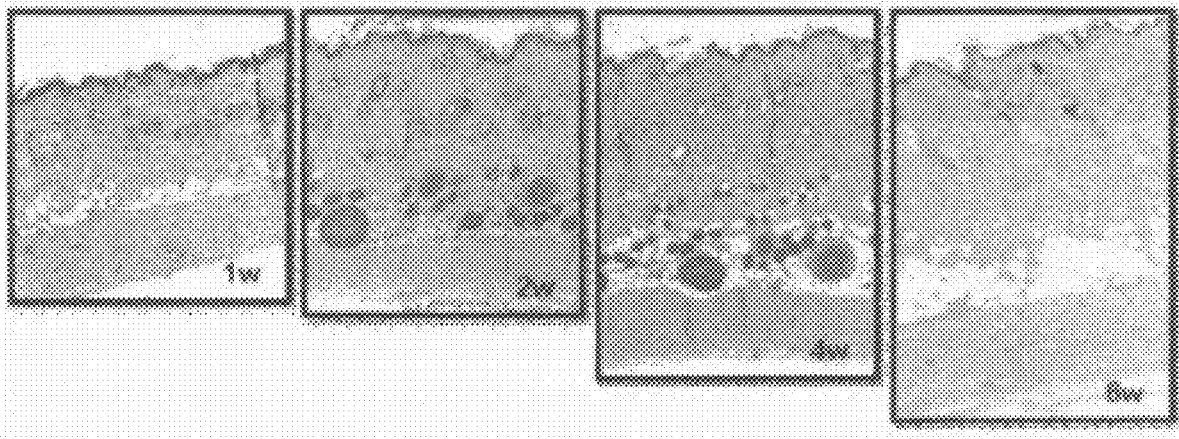
FIG. 5 is a picture, which is taken through an optical microscope, and shows collagen over time after a colloidal aqueous solution is injected.
Figure 7:
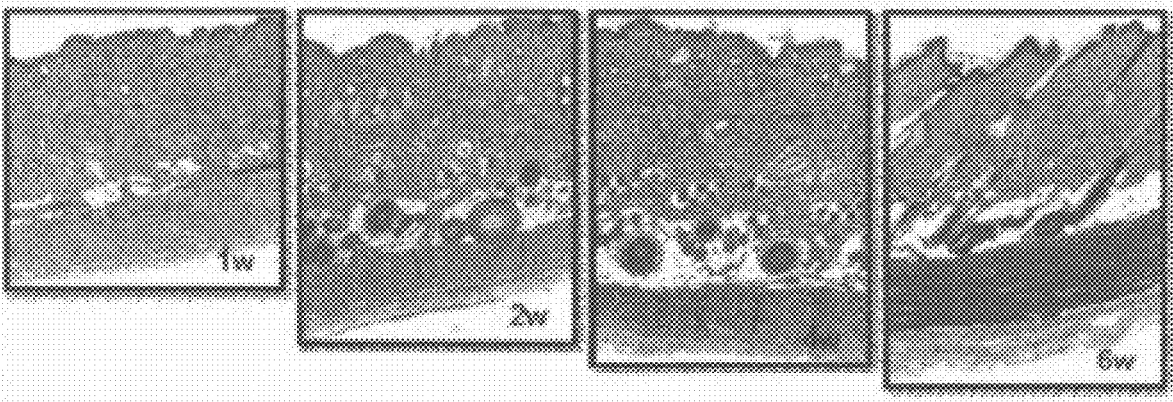
FIG. 7 is a picture, which was taken through an optical microscope, and shows collagen over time after PBS is injected.

FIG. 3 is a picture which is taken with DSLR (D3000, Nikon, Japan) to confirm whether samples are leaked after PBS and a colloidal aqueous solution are injected; FIG. 4 is a picture, which is taken through an optical microscope, and shows a skin thickness over time after a colloidal aqueous solution is injected; and FIG. 5 is a picture, which is taken through an optical microscope, and shows collagen over time after a colloidal aqueous solution is injected. In addition, FIG. 6 is a picture, which is taken through an optical microscope, and shows a skin thickness over time after PBS was injected; FIG. 7 is a picture, which is taken through an optical microscope, and shows collagen over time after PBS is injected; and FIG. 8 is a graph showing a skin thickness over time after PBS and a colloidal aqueous solution are injected.

Referring to FIG. 3, when being observed immediately after injecting PBS and the colloidal aqueous solution, it may be identified that the samples are not leaked.

Referring to FIGS. 4, 6, and 8, as a result of histopathological evaluation with H&E stain, it may be identified that the thickness of subcutaneous layer in the tissue subcutaneous layer in which the colloidal aqueous solution is injected also increases as the colloidal aqueous solution is injected over time up to six weeks, and it can be seen that an amount of increase according to this is certainly improved relative to FIG. 6 in which PBS is injected.

Referring to FIGS. 5 and 7, as a result of histopathological evaluation with MT stain, it may be identified that the collagen formation in the tissue subcutaneous layer in which the colloidal aqueous solution is injected is identified, and the thickness of subcutaneous layer according to the collagen formation also increases over time up to six weeks, and it can be seen that an amount of increase according to this is certainly improved relative to FIG. 7 in which PBS is injected.

Further, referring to FIGS. 4-7, when evaluating foreign substance reaction according to Table 4 above, it is identified that a significant foreign substance reaction due to the colloidal aqueous solution injection is not observed, and inflammatory cells, lymphocytes, and macrophages in a fibrous tissue are hardly seen (Score 1), and there is no difference in foreign substance reaction compared with before the colloidal aqueous solution injection.

As such, when meeting a concentration, HLB, and K value according to the present invention, a tissue restoration composition using a non-toxic biocompatible polymer and a method for manufacturing the same may be provided.

Hitherto, the preferred examples of the present invention have been described with reference to figures. Although the examples of the present invention have been disclosed for illustrative purposes, those skilled in the art will appreciate that various modifications, additions, and substitutions are possible, without departing from the technical idea or essential features of the present invention.

Accordingly, the scope of the present invention is defined by the following claims rather than the detailed description of the examples. It shall be understood that all modifications or changes in forms conceived from the meaning and scope of the claims and their equivalents are included in the scope of the present invention.

The invention claimed is:

1. A tissue restoration composition in colloidal phase, comprising a copolymer in which a hydrophobic biocom- patible polymer and a hydrophilic biocompatible polymer are polymerized and which is dispersed in water, wherein the colloidal phase is prepared by adding the copolymer to water, followed by heating to a temperature between a melting point of the copolymer and a boiling point of the water, and wherein the colloidal phase has a viscosity of 20-200,000 cP, wherein the hydrophobic biocompatible polymer is at least any one polymer selected from the group consisting of polyglycolic acid, polycaprolactone, poly lactic acid, polydioxanone, poly(trimethylene carbonate), polyhydroxybutyrate, and a copolymer including the same, and wherein the hydrophilic biocompatible polymer is at least any one polymer selected from the group consisting of methoxy polyethylene glycol, dihydroxy polyethylene glycol, mono-alkoxy polyethylene glycol, and polyethylene glycol, wherein the concentration of the copolymer in a colloidal solution is 10-50 wt %, and wherein the hydrophilic biocompatible polymer has molecular weight of 5,000-50,000 g/mol, the hydrophobic biocompatible polymer has molecular weight of 5,000-50,000 g/mol, and the copolymer has molecular weight of 10,000-120,000 g/mol.

2. The tissue restoration composition of claim 1, wherein the composition has a range of K factor represented by the following equation 1 is 0.01-5:

$$K=(m_{100}*M_h^{2}*10)/(M_1*\text{HLB}^2) \qquad \text{<Equation 1>}$$

where $m_{100}$ is the number of moles of polymers in 100 g of an aqueous solution, $M_h$ is the molecular weight of a hydrophilic part, $M_1$ is the molecular weight of a hydrophobic part, and HLB is represented by the following equation 2, $$\text{HLB}=20*M_h/M \qquad \text{<Equation 2>}$$

where $M_h$ is the molecular weight of the hydrophilic part, and M is the total molecular weight.

3. The tissue restoration composition of claim 1, wherein the value of HLB is 0.1-20 in the equation 2.

4. The tissue restoration composition of claim 1, wherein the bonding structure of the copolymer comprises the structure of the following formula 1, formula 2, or formula 3:

X—Y         [Formula 1]

Y—X—Y         [Formula 2]

X—Y—X         [Formula 3]

where X is the hydrophilic biocompatible polymer, and Y is the hydrophobic biocompatible polymer.

5. The tissue restoration composition of claim 1, wherein the colloidal phase has no change or an increase in turbidity when water is added.

6. The tissue restoration composition of claim 1, wherein the colloidal phase is prepared by adding the copolymer to water and the water has a temperature lower than the melting point of the copolymer.

\* \* \* \* \*